(12) United States Patent
Harlan et al.

(10) Patent No.: US 10,145,055 B1
(45) Date of Patent: Dec. 4, 2018

(54) APPARATUS AND METHODS FOR ULTRAVIOLET LIGHT TREATMENT OF LAUNDRY

(71) Applicant: Cliff Shirp Enterprises, LLC, Scottsdale, AZ (US)

(72) Inventors: Laurence Harlan, Scottsdale, AZ (US); Yoram Weiss, Cherry Hill, NJ (US); Roger P. Wiesenauer, Las Vegas, NV (US); Oren Weiss, Cherry Hill, NJ (US)

(73) Assignee: Cliff Shirp Enterprises, LLC, Scottsdale, AZ (US)

( * ) Notice: Subject to any disclaimer, the term of this patent is extended or adjusted under 35 U.S.C. 154(b) by 393 days.

(21) Appl. No.: 14/969,859

(22) Filed: Dec. 15, 2015

Related U.S. Application Data

(63) Continuation-in-part of application No. 14/729,225, filed on Jun. 3, 2015.

(60) Provisional application No. 62/006,962, filed on Jun. 3, 2014.

(51) Int. Cl.
| | |
|---|---|
| *D06F 58/20* | (2006.01) |
| *A61L 2/10* | (2006.01) |
| *A61L 2/28* | (2006.01) |

(52) U.S. Cl.
CPC .............. *D06F 58/203* (2013.01); *A61L 2/10* (2013.01); *A61L 2/28* (2013.01)

(58) Field of Classification Search
CPC ........ D06F 37/10; D06F 37/28; D06F 58/203; A61L 2/08; A61L 2/10; A61L 2/28
See application file for complete search history.

(56) References Cited

U.S. PATENT DOCUMENTS

| | | | | |
|---|---|---|---|---|
| 5,664,340 | A * | 9/1997 | Brown ...................... | A61L 2/10 34/275 |
| 6,088,932 | A * | 7/2000 | Adamski ................. | D06F 58/26 34/274 |
| 6,877,248 | B1* | 4/2005 | Cross .................... | D06F 58/203 34/275 |
| 2006/0163135 | A1* | 7/2006 | Ellis ....................... | D06F 35/001 210/251 |
| 2011/0057123 | A1* | 3/2011 | Ho .......................... | H02J 7/025 250/492.1 |

FOREIGN PATENT DOCUMENTS

KR    20110039985 A  *  4/2011

* cited by examiner

*Primary Examiner* — David E Smith
(74) *Attorney, Agent, or Firm* — Etherton Law Group, LLC

(57) ABSTRACT

An apparatus for exposing laundry to ultraviolet (UV) light comprises a mobile unit having a housing and at least one UV light carried by the housing and directed exteriorly therefrom. An activation module is located in the housing and configured to supply electrical power to the at least one UV light only when at least one activation criterion is satisfied. A battery power unit located in the housing supplies the electrical power to the at least one UV light via the activation module. The mobile unit can be connected to a base unit located on an interior surface of a laundry machine door. A UV light-sensitive laundry sheet can be used to gage UV light exposure to the laundry.

9 Claims, 6 Drawing Sheets

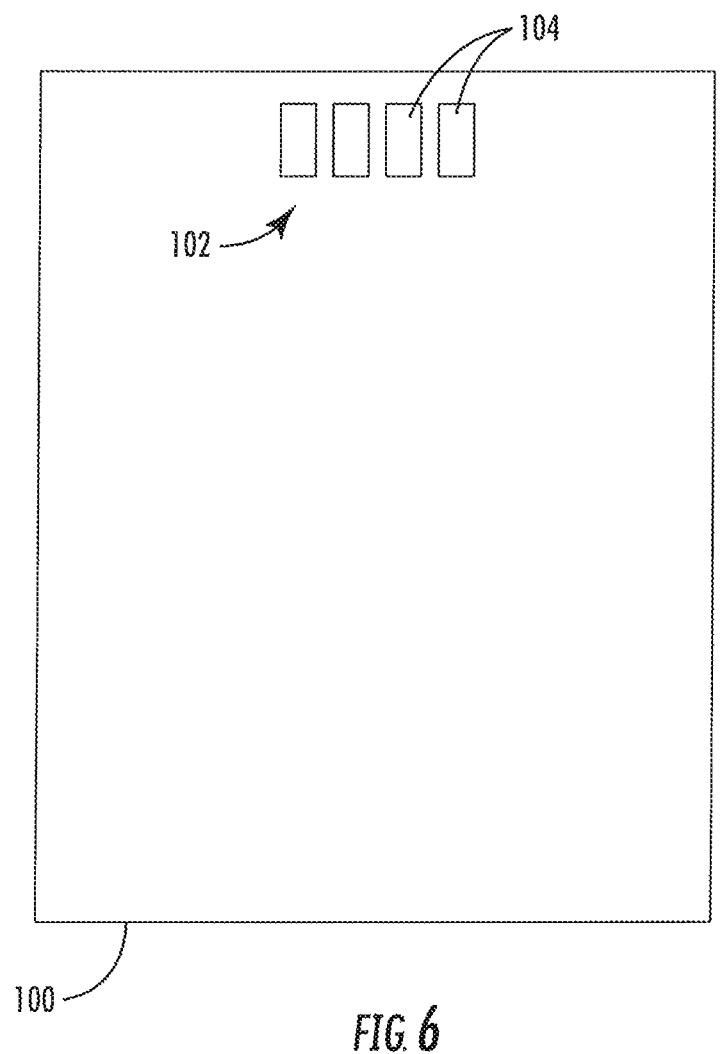

APPARATUS AND METHODS FOR ULTRAVIOLET LIGHT TREATMENT OF LAUNDRY

FIELD OF THE INVENTION

The present invention relates to apparatus and methods for sanitizing or disinfecting laundry, and more particularly, to dryer apparatus that generate ultraviolet (UV) light and related methods and products.

BACKGROUND OF THE INVENTION

While regular clothes washing will remove most dirt and stains from clothing, it is often inadequate to kill bacteria and other infectious disease agents that may be carried by the clothes. This is particularly the case where cold water washing cycles are used, which are more frequent in modern, energy-saving, washing machines. To address this problem, it has previously been proposed to expose clothes to UV light during some point of the washing and/or drying cycle.

There is a potential for eye damage with direct exposure to a UV light source, however. As a consequence, many prospective users would be reluctant to use a UV light device in a laundry ball form, which is highly portable and might easily be obtained by an unauthorized user, like a small child. Additionally, given the very dynamic environment inside laundry machines, it can be difficult to determine when adequate UV light exposure has occurred for a desired sanitization or disinfection effect. Thus, while UV light offers a potential benefit in the area of disinfecting clothes, further improvements are possible.

SUMMARY OF THE INVENTION

In view of the foregoing, it is an object of the present invention to provide improved apparatus and related methods and products for UV treatment of laundry. According to an embodiment of the present invention, an apparatus for exposing drying clothes to ultraviolet (UV) light comprises a mobile unit having a housing and one or more UV lights carried by the housing and directed exteriorly therefrom. An activation module is located in the housing and configured to supply electrical power to the UV lights only when at least one activation criterion is satisfied. A battery power unit located in the housing supplies the electrical power to the UV lights via the activation module. The mobile unit can be connected to a base unit located on an interior surface of a laundry machine door. A UV light-sensitive laundry sheet can be used to gage UV light exposure to the laundry.

These and other objects, aspects and advantages of the present invention will be better appreciated in view of the drawings and following detailed description of preferred embodiments.

BRIEF DESCRIPTION OF THE DRAWINGS

FIG. 6 is a plan view of a laundry sheet for use in connection with the UV light assembly of FIG. 1.

DETAILED DESCRIPTION OF PREFERRED EMBODIMENTS

Figure 1:
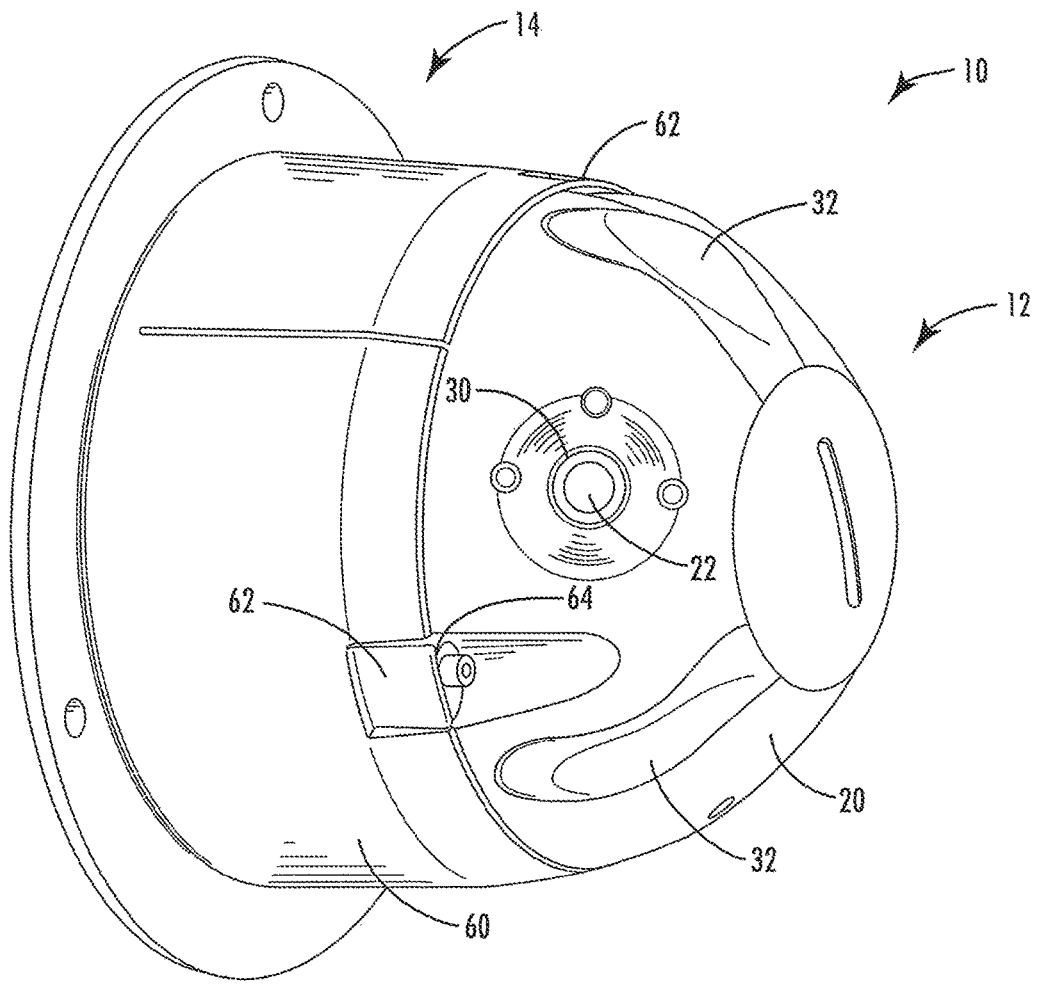
FIG. 1 is a perspective view of a UV light assembly including a mobile unit and a base unit, according to an embodiment of the present invention.
Figure 2:
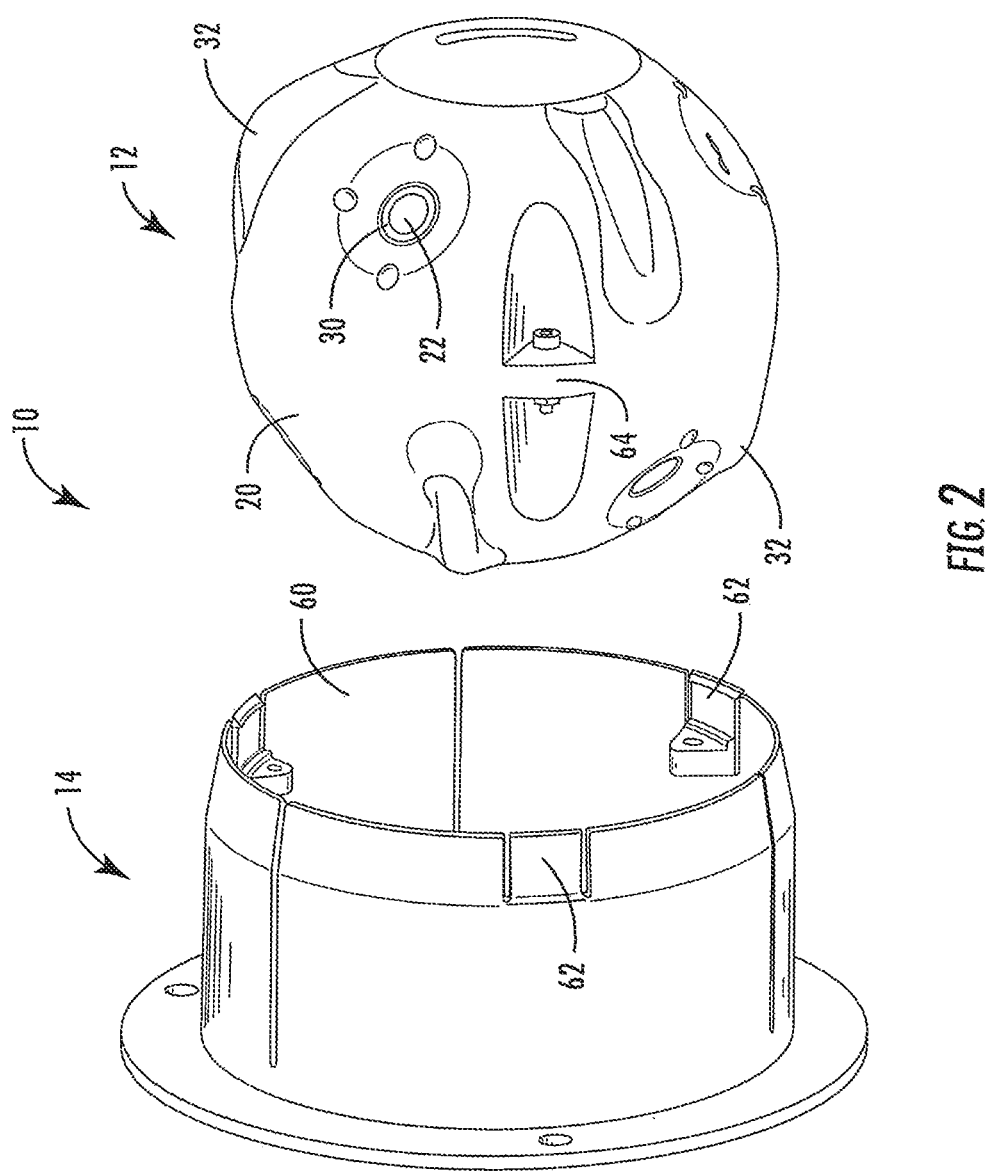
FIG. 2 is a partially exploded perspective view of the UV light assembly of FIG. 1.
Figure 3:
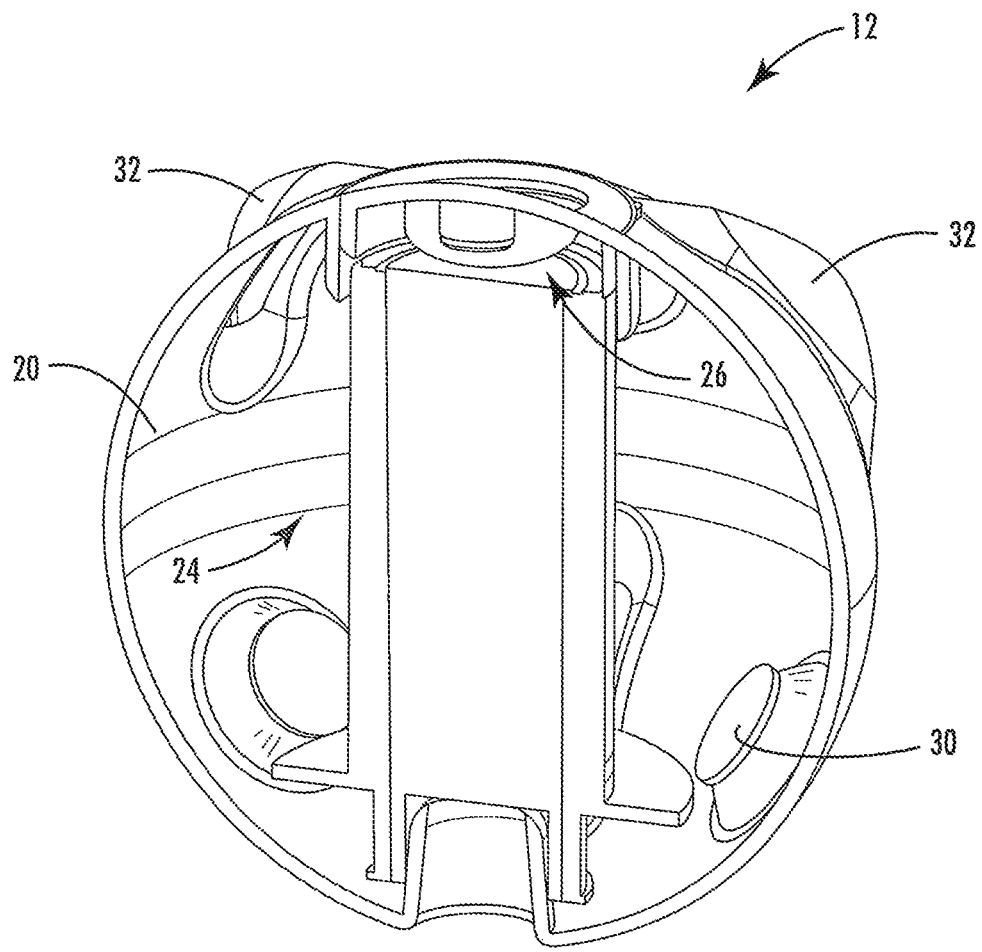
FIG. 3 is a sectional view of the mobile unit of FIG. 1.
Figure 4:
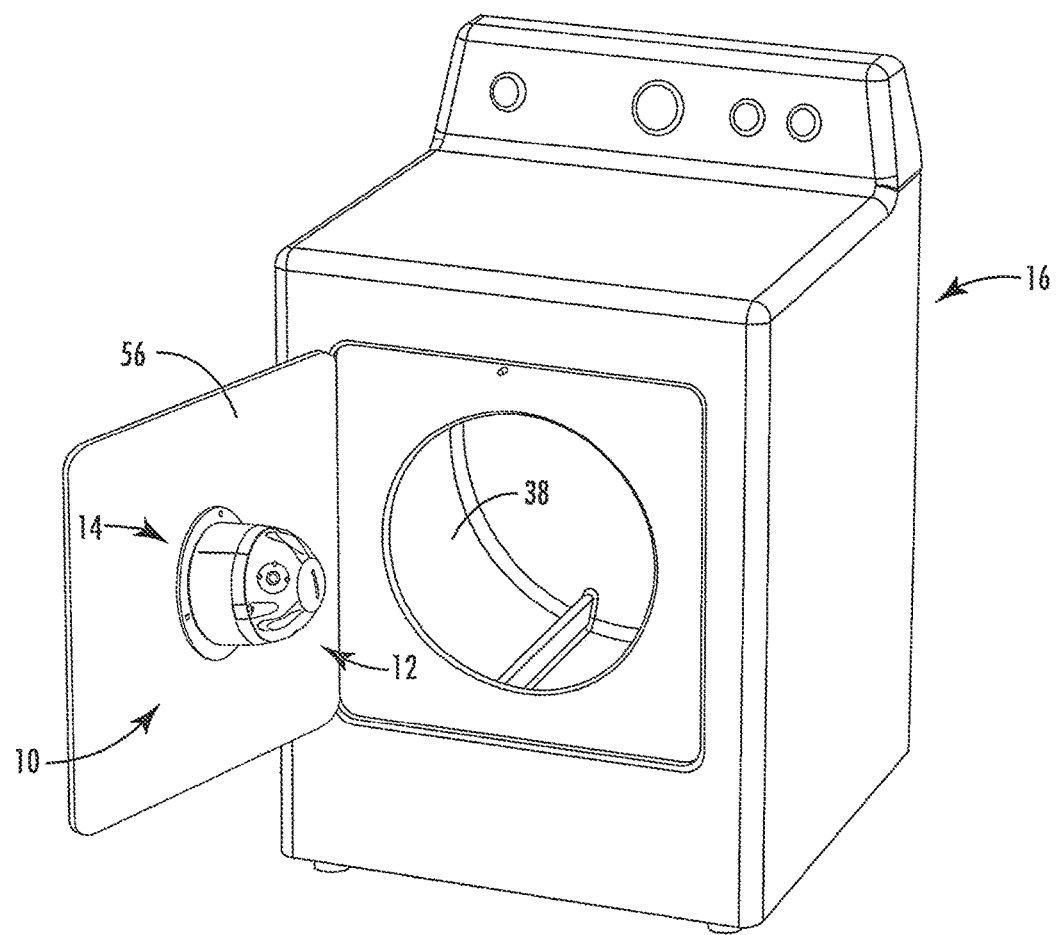
FIG. 4 is a perspective of view of the UV light assembly of FIG. 1 installed on a laundry machine.
Figure 5:
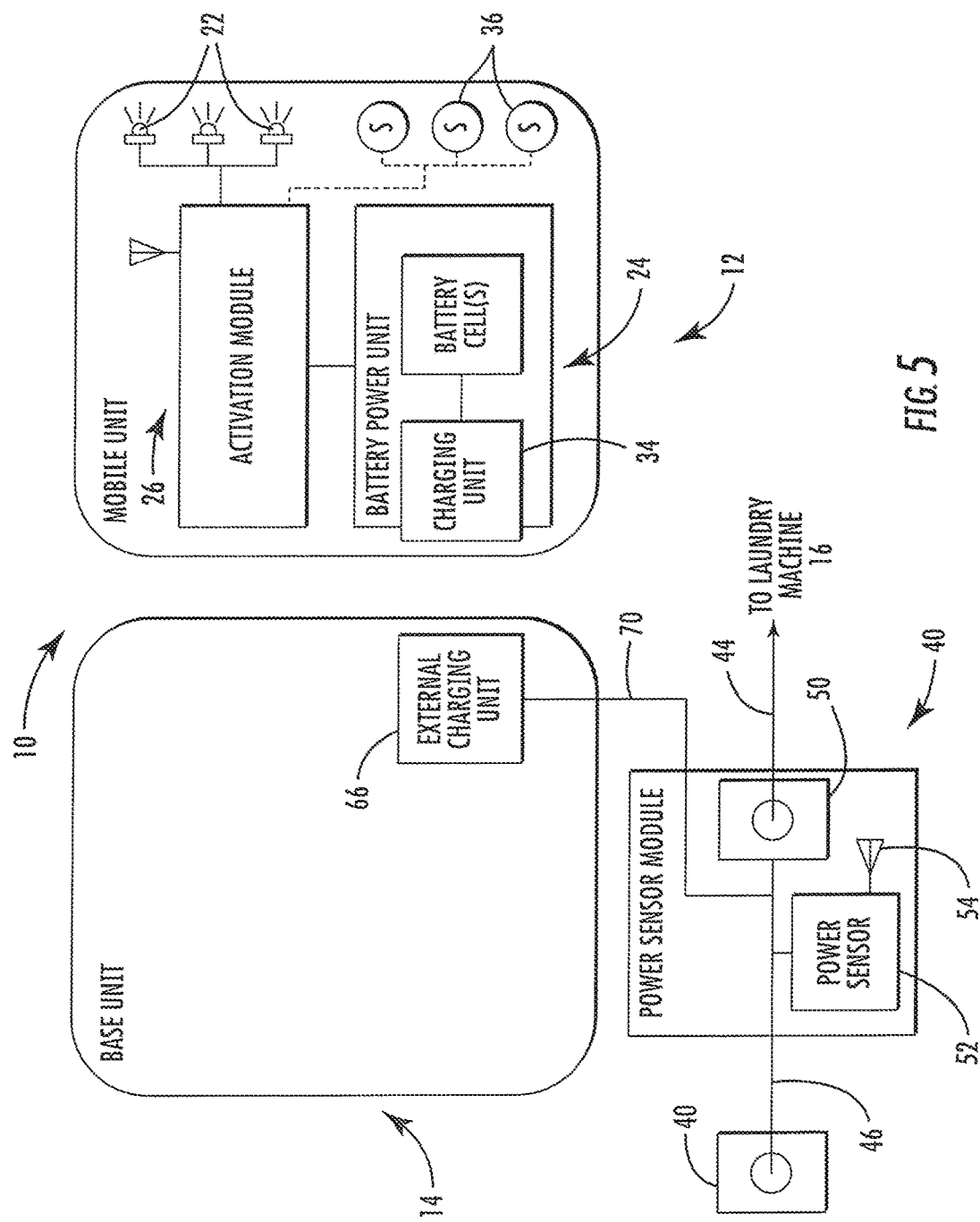
FIG. 5 is a circuit schematic of the UV light assembly of claim 1.

According to an embodiment of the present invention, referring to FIGS. 1-3, a UV light assembly 10 includes a mobile unit 12 and a base unit 14. The base unit 14 is mounted inside a laundry machine 16 (see FIG. 4), such as a dryer, with the mobile unit 12 releasably connected thereto. Referring also to FIG. 5, the mobile unit 12 has a housing 20 carrying a plurality of UV lights 22 oriented to direct light exteriorly thereto, with a battery power unit 24 supplying power to the UV lights 22 via an activation module 26, as will be explained in greater detail below. Laundry treatment with UV light is effected via the lights 22, with the mobile unit 12 either remaining connected to the base unit 14, or tumbling freely with clothes within the laundry machine 16.

The housing 20 is advantageously a watertight shell defining a plurality of transparent openings 30 and having one or more tactile protuberances 32 extending therefrom to help the mobile unit 12 be carried along with the laundry when detached from the base unit 14, and to cushion impacts with hard surfaces within the laundry machine 16. The UV lights 22, battery power unit 24 and activation module 26 are arranged within the housing 20, with the UV lights 22 being directed through the openings 30.

Light emitting diodes (LEDs) configured to emit UV lights are preferably employed as the UV lights 22. The size, power consumption and heat generation of UV LEDs are believed to be optimal for utilization in a mobile unit like the mobile unit 12.

At its simplest, the battery power unit 24 includes one or more battery cells that can be removed for charging or replacement via a watertight opening in the housing 20. Advantageously, the battery power unit 24 incorporates an internal charging unit 34 that receives power through the housing 20 via a charging connection. Preferably, the internal charging unit 34 interacts with the base unit 14, such that battery charging occurs automatically when the mobile unit 12 is seated in the base unit 14. Inductive charging, or other charging means suitable for use in wet environments, are optimal. A charging unit located outside the laundry machine 16 could also be provided.

The activation module 26 is configured to control the supply of electrical power to the UV lights 22 from the batter power unit 24, such that the UV lights 22 are de-energized whenever one or more activation criteria is not met. The activation module 26 can be realized digitally with a microprocessor, via analog switches, or a combination of the two.

Advantageously, there are multiple activation criteria including, for instance, at least one "internal" criterion sensed by one more sensors 36 of activation module 26 in or on the mobile unit 12 and at least one "external" criterion related to the operation of the laundry machine 16 sensed externally to the mobile unit 12 and communicated thereto. Alternately, only internal or external activation criteria could be used.

One example of an internal criterion is mobile unit 12 motion. The sensors 36 would include a motion sensor, and the motion criterion is met only when the motion sensor detects motion corresponding to movement with a laundry machine for a predetermined period of time. Any lack of motion deemed to constitute an interruption in the laundry machine movement would result in the motion criterion not being met. The motion criterion could include a bypass that is activated when the mobile unit 12 was mounted in the base unit 14, such that the motion criterion would no longer need to be satisfied to supply power to the UV lights 22.

The motion criterion could also employ a motion sensor that actively detected the motion of a moving portion of the laundry machine 16, such as a dryer drum. Such a motion criterion would only be met when motion was detected above a threshold indicating normal operation, and would no longer be met when motion dropped below such a threshold.

Another example of an internal criterion is a proximity criterion. The sensors 36 include a proximity sensor, such as a passive radio frequency identification (RFID) circuit, that is effective to determine whether the mobile unit 12 is outside a predetermined distance from the base unit 14 or other UV light assembly 10 or laundry machine 16 component. The proximity criterion would only be met when the mobile unit 12 was determined to be within the predetermined distance.

A further example of an internal criterion is a light criterion. The sensors 36 include a photo sensor to detect visible light above a threshold that would not be detected within an operating laundry machine 16. The light criterion is not met whenever light levels above the threshold are sensed.

An example of an external criterion is a laundry machine power criterion. An external sensor detects an electrical power consumption of the laundry machine 16 to determine whether or not a rotating drum 38 or other moving component of the machine is in motion. The power criterion is not met if the power consumption, which could be sensed in terms of current, voltage, etc., drops below a power threshold indicative that power to the drum has been secured. The term "drum" is used generically herein to refer to a moving part of a laundry machine, the delivery of power to which is indicative of laundry machine operation (e.g., a powered agitator would also be considered a "drum" pursuant to this definition).

Where the UV light assembly 10 is retrofit into an existing laundry machine 16, a power sensor module 40 is connected between an electrical outlet 42 and a power cord 44 of the laundry machine 16. For instance, the power sensor module 40 includes a power cord 46 that plugs into the outlet 42 and a socket 50 into which the power cord 44 is plugged. A power sensor 52 in the power sensor module 40 detects the electrical power drawn by the laundry machine 16. If the power criterion is met, a transmitter 54 located in the power sensor module 40 and/or base unit 14 wirelessly continuously transmits a positive external criterion indication to the activation module 26 in the mobile unit. If the power criterion is not met, then the positive indication is no longer transmitted. When the activation module 26 no longer receives the positive indication, then power to the UV lights 22 is secured (if not previously secured based on other criteria).

The UV light assembly can be built into a laundry machine and receive power consumption information from the power supply circuitry of the machine. Alternately, or additionally, other machine-sensed indicators of non-operation could be used; for instance, machine door 56 position. In either case, when the external criterion is not met, transmission of the positive indication to the base unit 14 would cease.

The base unit 14 defines a mobile unit receptacle 60 with a plurality of retention elements 62, such as clips, that engage mating surfaces 64 on the housing 20 of the mobile unit 12. Where the base unit 14 is equipped to charge the battery power unit 24, the base unit 14 also includes an external charging unit 66 for interfacing with the internal charging unit 34.

Advantageously, the base unit 14 is centrally mounted on the inside of the door 56 of the laundry machine 16. Where the base unit 14 is manufactured with the laundry machine 16 and supplied with electrical power, power to the base unit 14 can be supplied from the power supply circuitry of the machine 16. Where a powered base unit 14 is retrofit into an existing laundry machine 16, the base unit receives power from the power sensor module 40 via a base unit cord 70. The cord 70 can be routed to the base unit 14 through an opening made through the door 56 or, particularly with a low profile cord, through the door 56 seal.

In operation, described with reference to laundry dryer, when loading the machine 16, a user decides whether to leave the mobile unit 12 attached to the base unit 14, or have it tumble with the laundry in the dryer drum. For instance, for most loads, the mobile unit 12 will be left free in the drum, but for large, bulky loads (e.g., comforters, mats, heavy towels, etc.), the mobile unit 12 will be left connected to the base unit 14. Whichever, the user chooses, the machine 16 is loaded, the door is closed and the machine 16 is started.

When the closed door and/or supply of power to the drum is detected, the positive indication is transmitted to the activation module 26 in the internal unit. Provided the motion criterion and/or any other internal criterion is met, the activation module 26 will supply power to the UV lights 22 from the battery power unit 24. As soon as any activation criterion is no longer met, the activation module 26 will secure power to the UV lights 22. When the laundry treatment with the UV light assembly 10 is done, the user removes the mobile unit 12 and, if detached, reinstalls the mobile unit 12 in the base unit 14, or other charging unit, for charging and storage.

Referring to FIG. 6, to aid a user in determining is adequate UV light exposure has been achieved, one or more UV sensitive laundry sheets 100 is loaded with the laundry. Each laundry sheet 100 is prepared with a UV light-sensitive medium that will appear, disappear, change color or otherwise undergo a visible change under exposure to UV light, with the medium applied such that a complete change will occur when a desired level of UV light exposure has occurred. In the depicted sheet 100, a discrete indicator area 102 is provided, with a plurality of markings 104 printed in UV light-sensitive ink. The markings 104 are calibrated such that they will change color at different rates to allow a user a quick visual indication of UV light treatment progress. When all markings 104 have changed color, then no further UV light exposure is needed. Alternately, the entire sheet 100 could be impregnated or otherwise printed with the medium, such that the visible change would affect the entire sheet 100. The sheet 100 can be advantageously employed with the UV light assembly 10 described above, or with other UV light treatment mechanisms.

The foregoing embodiments are provided for illustrative and exemplary purposes, the present invention is not necessarily limited thereto. Those skilled in the art will appreciate that various modifications, as well adaptations for particular circumstances, will fall within the scope of the invention as herein shown and described and of the claims appended hereto.

What is claimed is:

1. An ultraviolet (UV) light assembly for laundry machine use, the assembly comprising:
   a mobile unit adapted for placement inside the laundry machine during operation thereof, the mobile unit including a housing and at least one UV light arranged to shine outwardly therefrom; and
   a power sensor module in communication with the UV light emitter, the power sensor including a module plug configured for receipt in a electrical outlet and a module receptacle configured to receive a laundry machine electrical plug therein, the power sensor module including power detection circuitry for determining an electrical power usage of the laundry machine;
   wherein the communication between the power sensor module and the UV light emitter is effective to automatically secure electrical power to the at least one UV light based on the electrical power usage of the laundry machine.

2. The assembly of claim 1, wherein the mobile unit is configured for free movement within a drum of the laundry machine and includes a battery power unit located in the housing for powering the at least one UV light, the mobile unit and the power sensor module being configured for wireless communication therebetween.

3. The assembly of claim 2, further comprising a base unit configured to releasably retain the mobile unit therein.

4. The assembly of claim 3, wherein the base unit is adapted for connection to a stationary interior surface of the laundry machine.

5. The assembly of claim 3, wherein the battery power unit includes a rechargeable battery and the base unit is configured to recharge the battery.

6. The assembly of claim 5, wherein the base unit is wired to the power sensor module and receives electrical power therefrom.

7. The assembly of claim 1, wherein the mobile unit is adapted for connection to a stationary interior surface of the laundry machine and receives electrical power through a wired connection.

8. The assembly of claim 7, wherein the mobile unit and the power sensor module are configured for wireless communication therebetween to effect the securing of electrical power to the at least one UV light.

9. The assembly of claim 1, wherein the mobile unit further includes a motion sensor configured to detect motion of at least one of the mobile unit and a drum of the laundry machine, the mobile unit being configured to automatically secure electrical power to the at least one UV light based on detected motion below a predetermined threshold.

* * * * *